US00PP33851P2

(12) United States Plant Patent
Hansen

(10) Patent No.: US PP33,851 P2
(45) Date of Patent: Jan. 11, 2022

(54) ***LEUCANTHEMUM* PLANT NAMED 'BANANA CREAM II'**

(50) Latin Name: ***Leucanthemum* x *superbum* (Bergmans ex J.W.Ingram) D.H.Kent**
Varietal Denomination: Banana Cream II

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,512

(22) Filed: Jul. 27, 2021

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
CPC ..... A01H 5/02; A01H 5/00; A01H 6/14
See application file for complete search history.

*Primary Examiner* — June Hwu

(57) ABSTRACT

The new Shasta daisy plant, *Leucanthemum* 'Banana Cream II', is a sturdy plant with dark-green serrated foliage and stiff stems. The numerous freely-flowering inflorescences producing two to three rows of ray florets starting light yellow and developing to creamy-colored. The center disk florets are golden yellow. Flowering repeats into fall if deadheaded. The new plant is useful in the landscape as a long-flowering border, in mass, as accent plants and containerized for patio or indoor use, or as a cut flower.

1 Drawing Sheet

Botanical classification: *Leucanthemum* x *superbum* (Bergmans ex J.W.Ingram) D.H.Kent.

Variety denomination: 'Banana Cream II'.

STATEMENT REGARDING PRIOR DISCLOSURES UNDER 37 CFR 1.77(B)(6)

The first non-enabling disclosure of the claimed plant was made by Walters Gardens, Inc. on Dec. 1, 2020 in the form of a website brief description and photograph followed by a short description and photograph in the "Walters Gardens 2021-2022 Catalog" by Walters Gardens, Inc first distributed on May 21, 2021. The first enabling disclosure of a sales of the claimed plant was on Aug. 3, 2020 by Walters Gardens, Inc. Walters Gardens, Inc. obtained the new plant and information about the new plant directly from the inventor. No plants of *Leucanthemum* 'Banana Cream II' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. and *Leucanthemum vulgare* with *Leucanthemum lacustre* (Broth.) Samp. and *Nipponanthemum nipponicum*. The new plant, *Leucanthemum* 'Banana Cream II' originated from a planned breeding program of the inventor at a wholesale perennial nursery in Zeeland, Mich., USA. The new *Leucanthemum* was a single plant selected from a group of seedlings from a cross on Jul. 15, 2015 between 'Sante' U.S. Plant Pat. No. 19,829 and 'Banana Cream' U.S. Plant Pat.

No. 23,181. The individual plant that eventually became 'Banana Cream II' was first evaluated in the summer of 2016 and originally given the breeder number 15-1-6 through the subsequent evaluations.

The present invention relates to a new and distinct cultivar of Shasta daisy botanically known as *Leucanthemum* x *superbum* and hereinafter referred to by the cultivar name 'Banana Cream II' or the new plant.

Asexual reproduction of the new cultivar by division at the same nursery in Zeeland, Mich. as the fall of 2017 has demonstrated that the new cultivar reproduces true to type with all of the characteristics of the original plant retained through successive generations of asexual propagation. The new plant has since been asexually propagated by basal shoot tip cuttings and sterile shoot tip tissue culture.

BRIEF SUMMARY OF THE INVENTION

The new plant, *Leucanthemum* 'Banana Cream II', is most closely compared to *Leucanthemum* 'Leumayel' U.S. Plant Pat. No. 19,242 and 'Banana Cream', 'Cream Puff' U.S. Plant Pat. No. 30,074, 'Snowcap' (not patented), 'Marshmallow' copending U.S. Plant Patent Application, 'Goldfinch' U.S. Plant Pat. No. 24,499 and 'Real Goldcup' U.S. Plant patent application Ser. No. 17/377,371.

'Leumayel' is slightly shorter in habit with less branching. In test trials in Zeeland, Mich., 'Cream Puff' has a shorter habit and has flowers that are less yellow. 'Snowcap' has smaller single inflorescences and shorter habit. 'Marshmallow' is shorter in habit and the inflorescences are double with more laciniate and less yellow ray floret ligules. 'Goldfinch' has shorter ray florets that are initially bright lemon yellow and lighten to ivory white. 'Real Goldcup' has shorter ray florets that are slightly more deeply emarginate.

'Sante' has smaller, flatter and less dome-shaped inflorescences with less yellow ray florets. 'Banana Cream' is later flowering, requires longer vernalization and has a more single inflorescence with ray florets that are less yellow and slightly shorter habit.

*Leucanthemum* 'Banana Cream II' differs from all cultivars known to the inventor in the following combined traits:

1. Sturdy, dense, mounded plants with green serrated foliage and stiff stems;
2. Inflorescence with two to three rows of ray florets.
3. Ray florets with ligules starting light yellow and remaining into maturity while initially flattened;
4. Center disk florets of golden yellow;
5. Ray floret ligules mature to creamy-colored;
6. Freely flowering habit and repeating if deadheaded;
7. Foliage is dark green.

BRIEF DESCRIPTION OF THE PHOTOGRAPHS

The photographs of 'Banana Cream II' demonstrate the overall appearance and landscape qualities of the new plant, including the unique traits planted in a full-sun trial garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
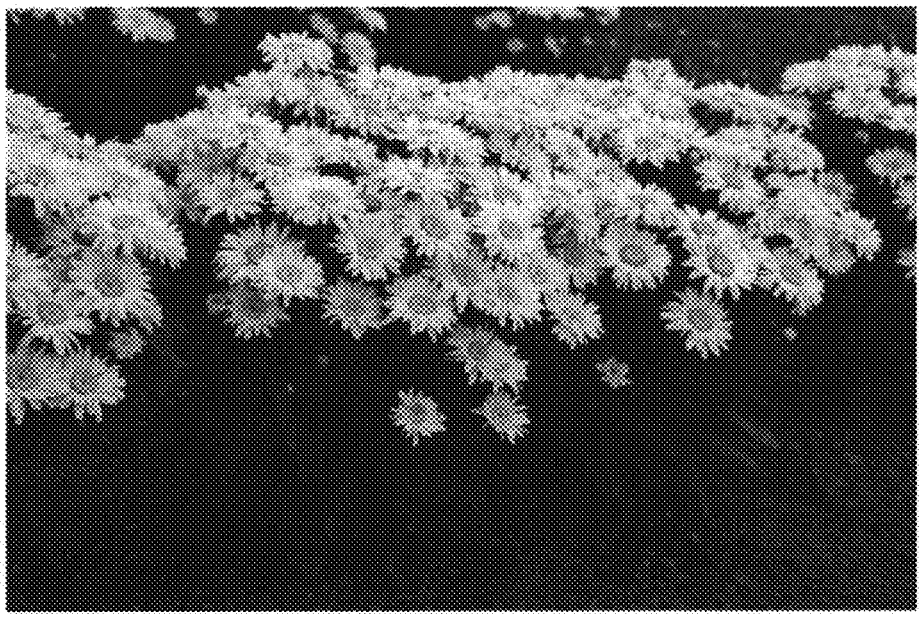
FIG. 1 shows a two-year-old new plant at peak flowering with inflorescences covering the plant from nearly top to ground.
Figure 2:
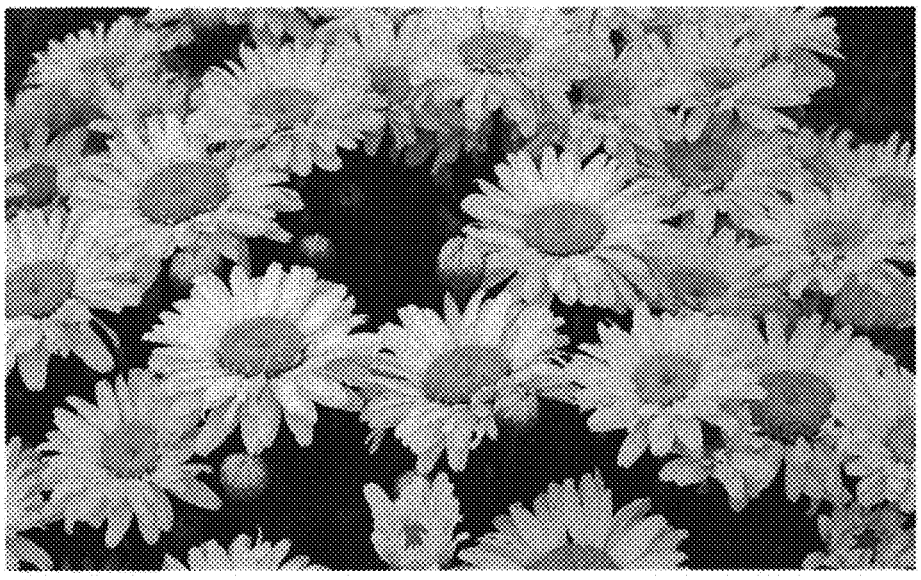
FIG. 2 shows a close-up of some the inflorescence and the buds at various stages.

The following descriptions and color references are based on the 2015 edition of The Royal Horticultural Society Colour Chart except where common dictionary terms are used. The new plant has not been observed in all possible environments and conditions. The phenotype of *Leucanthemum* 'Banana Cream II' may vary with different growing conditions such as changes in temperature, light intensity, water availability, fertility, but without change in the genotype.

The plants used for description purposes were two-year-old and were grown in Zeeland, Mich. in a full-sun, loamy-sand trial plot environment with supplemental water and limited fertilizer as needed and also a partially-shaded greenhouse. Summer temperatures range from night lows of about 10° C. to daytime highs of about 34° C. Measurements and numerical values represent averages or ranges of trial plants.

Botanical classification: *Leucanthemum* x *superbum;*

Parentage: Female is 'Sante', male parent is 'Banana Cream';

Habit: Herbaceous perennial with about 28 to 36 branched stems arising from rhizome base; each stem having four to eight inflorescences each; about 56 cm tall and 44 cm across with rounded top and sides;

Roots: Fibrous, thin, heavily branched; root color nearest RHS 155D depending on soil type;

Propagation: Tip cuttings or tissue culture; about two weeks to produce roots from cutting; about 33 weeks to finish to flower in 3.8 liter pot depending on season;

Stems: About 28 to 36 main stems per plant; strong; mostly upright; canaliculated; hispidulous; terete, hollow in distal portion; 9.0 mm diameter at base; to 52 cm tall; about 13 nodes before flowers; average internode length about 3.0 cm;

Stem color: Nearest RHS 146B with channels nearest RHS 137B;

Axillary branches: Four to eight; between 6.0 to 12.0 cm long and 4.0 to 6.0 mm diameter; upright to angles of about 30° or less from main stem; side flowers rising above initial flower;

Axillary branch color: Nearest RHS 146B with channels nearest RHS 137B;

Leaves: Lanceolate to linear; apex acute; base attenuate; alternate; sparsely puberulent adaxial and abaxial; margin serrate and ciliolate with seven to nine teeth per side, and size average about 3.0 mm long and 3.0 mm wide; nearly microscopically micro-ciliolate; lowest leaves to about 12.5 cm long and 3.8 cm wide, average about 8.2 cm long and 3.2 cm wide; no fragrance detected;

Leaf color: Young adaxial between RHS 137A and RHS 137B distally and nearest RHS 144A proximally, abaxial nearest RHS 137B distally and RHS 144A proximally; mature adaxial nearest RHS NN137A, abaxial nearest RHS 144A;

Veins: Anastomosing; glabrescent adaxial and puberulent to pubescent abaxial; adaxial slightly raised, abaxial midrib costate and secondary veins smooth;

Vein color: Adaxial midrib nearest RHS 145D proximally and distally midrib and secondary veins nearest RHS 137B; abaxial midrib nearest RHS 145D and secondary veins nearest RHS 137B;

Inflorescence: Capitate; about 80 per plant at one time; primary inflorescence 11.0 cm across and 4.5 cm tall; comprising two or three outer rows of large ray florets and about 450 to 550 central disk florets; individual inflorescence lasting about three weeks on or cut from plant; upright;

Fragrance: Faint dirty fragrance detected;

Flowering period: Early summer (late June) to early autumn in Michigan if deadheaded;

Peduncle: Strong, stiff; hispidulous to puberulent; cylindrical; longitudinally fluted; 6.0 to 50.0 cm long and about 9.0 mm diameter at base; upwardly;

Peduncle color: Nearest RHS 146B with channels nearest RHS 137B;

Bud: With ray florets still vertical — oblong globose, 3.5 cm across ray florets and 2.2 cm from base of phyllaries to apex of capitulum;

Bud color of greenhouse grown plant: Adaxial and abaxial ray floret ligule nearest RHS 1D distally, central portion nearest RHS 1A adaxial and RHS 2B abaxial, base nearest RHS 146C; phyllaries nearest RHS 138A in center and margin nearest RHS 196D;

Bud color of full sun grown plant: Adaxial and abaxial ray floret ligule nearest RHS 3A distally, central portion nearest RHS 1D adaxial and RHS 3D abaxial, base nearest RHS 146D; phyllaries nearest RHS 138A in center and margin nearest RHS 196D;

Floret type: Ray florets on the exterior two to three rows, disk florets in inflorescence center;

Ray florets: To about 64 per inflorescence; arranged around outer perimeter of capitulum in two to three rows; ligules glabrous adaxial and abaxial, base attenuate rolled into tube, apex emarginate with typically two notches indented to about 0.5 mm, margin entire; to about 46.0 mm long and 11.0 mm wide; typically flat, but occasionally reflex in distal 5 mm;

Disk florets: Tubular; to about 450 to 550 per inflorescence, at center of capitulum; combined inflorescences disk to about 32.0 mm across and about 12.0 mm tall; individual floret about 10.5 mm tall and 2.5 mm wide, five tepals, about 8.5 mm long; with acute apex, fused in basal 6.5 mm;

Ray floret color greenhouse grown: When ray floret ligules first horizontal adaxial between RHS 2D and RHS 4D in middle portion, apex between RHS 2A and RHS 2B, base between RHS 146D and RHS 144A, abaxial middle portion nearest RHS 4D, apex nearest RHS 3B and base nearest RHS 146C; mature adaxial and abaxial ligules nearest RHS NN155A in middle portion, adaxial apex nearest RHS 4C and abaxial apex nearest RHS 4A, base between RHS 146D and RHS 144A;

Ray floret color full sun grown: When ray floret tepals first horizontal adaxial ligules middle portion nearest RHS 2D, abaxial middle portion nearest RHS 4D, adaxial apex nearest 4B and abaxial apex nearest RHS 4A, basal 5 mm nearest RHS 144A; mature adaxial ligules between RHS 155D and RHS 8D and abaxial nearest RHS NN155B in the middle portions, 1.0 mm apices adaxial and abaxial nearest RHS 5D and basal 5.0 mm nearest RHS 146D;

Disk floret color: Young adaxial and abaxial corolla tube nearest RHS 14B in distal 1 mm, next distal 2 mm transparent, corolla tube base between RHS 146D and RHS 145A; mature adaxial and abaxial corolla tube nearest RHS 14B distally, center transparent and base RHS 146D and RHS 145A;

Androecium: Five stamens connate around style;

*Anther*.—Five; connate into tube; about 3.0 mm long and less than one mm wide, not present in ray florets, functional in disk florets; coloration nearest RHS 17B.

*Filaments*.—Fused together at apex, 3.0 mm to 4.0 mm long and less than 0.1 mm diameter, filament coloration translucent to nearest RHS 145D.

*Pollen*.—Only found in disk florets; color nearest RHS 21A.

Gynoecium: In ray florets and disk florets; to about 10.0 mm long; exserted;

*Style*.—About 6.0 mm long and less than 0.3 mm diameter, split and curved at apical 1.0 mm; color nearest RHS 145D.

*Stigma*.—Bifid; to about 1.5 mm long and less than 0.5 mm diameter; color nearest RHS 9C.

Involucre: Made of about three layers of phyllaries; to 4.0 cm across and 1.0 cm tall;

Phyllaries: Lanceolate; adaxial and abaxial glabrous, matte; margin micro-erose and transparent; apex acute; base truncate; to about 44 per head arranged in about three imbricate rows; 11.0 mm long and 4.0 mm wide;

Phyllaries color: Adaxial and abaxial identical, outer 1.0 mm of margin transparent, next inner 0.5 mm with veins into transparent margin nearest RHS N199B, next 1.0 mm between RHS 145A and RHS N144A with center nearest RHS 137B;

Fruit: Achene, pointed at base and rounded at distal end with longitudinal color striations nearest RHS N200A and lighter than RHS 155D; about 3 to 4 mm long and 1.5 mm across;

*Leucanthemum* 'Banana Cream II' grows best with adequate moisture but can tolerate some dryness once established. Vernalization is not required for flowering but is beneficial. The new plant is tolerant of high temperatures of at least 36° C. and cold hardy to at least USDA zone 5 as well as strong wind and rain. Other disease or pest resistance beyond that common to Shasta daisy has not been observed.

I claim:

1. The new and distinct Shasta daisy plant *Leucanthemum* 'Banana Cream II' as herein shown and described.

* * * * *